United States Patent [19]

Sakai

[11] 4,369,780
[45] Jan. 25, 1983

[54] BLOCKING CONDITION DETECTION DEVICE IN A MEDICAL FLUID INJECTION SYSTEM

[75] Inventor: Eiichi Sakai, Nara, Japan

[73] Assignee: Sharp Kabushiki Kaisha, Osaka, Japan

[21] Appl. No.: 180,388

[22] Filed: Aug. 21, 1980

[30] Foreign Application Priority Data

Aug. 24, 1979 [JP] Japan .................. 54-108489

[51] Int. Cl.³ ............................................ A61M 5/00
[52] U.S. Cl. ...................... 128/214 E; 128/DIG. 12; 200/81.9 R; 417/38
[58] Field of Search ....... 128/214 E, 214 F, DIG. 12, 128/DIG. 13; 335/205, 207; 116/70, 270; 200/81.9 M, 82 E, 83 L, 81 R, 81.9 R; 210/90; 417/474-478, 38, 412, 63

[56] References Cited

U.S. PATENT DOCUMENTS

| | | | |
|---|---|---|---|
| 2,719,889 | 10/1955 | Miller | 200/81.9 R |
| 3,306,229 | 2/1967 | Snythe | 417/475 X |
| 3,397,372 | 8/1968 | Maxwell | 335/205 |
| 3,611,220 | 10/1971 | Hoffman | 335/207 |
| 3,731,680 | 5/1973 | Wright et al. | 128/214 F X |
| 3,942,526 | 3/1976 | Wilder et al. | 128/214 E |
| 4,134,407 | 1/1979 | Elam | 116/270 X |
| 4,194,974 | 3/1980 | Jonsson | 128/214 F X |
| 4,277,226 | 7/1981 | Archibald | 128/214 F X |
| 4,277,227 | 7/1981 | Jenkins | 417/63 |
| 4,309,993 | 1/1982 | Brown | 128/214 E |

FOREIGN PATENT DOCUMENTS 1223024  8/1966  Fed. Rep. of Germany ..... 200/81.9 R

*Primary Examiner*—Dalton L. Truluck
*Attorney, Agent, or Firm*—Birch, Stewart, Kolasch & Birch

[57] ABSTRACT

A medical fluid injection system which includes a flexible conduit and a rotor for supplying a pressurized medical fluid to the human body through the flexible conduit. A blocking condition detection unit is provided for detecting an abnormal blocking condition of the flexible conduit. The blocking condition detection unit includes a supporting member for supporting the flexible conduit in a manner that the section of the flexible conduit is forced to show a rectangular configuration. A rod is slidably disposed through the supporting member so that one end of the rod makes contact with the flexible conduit. When an abnormal blocking condition occurs in the flexible conduit, the flexible conduit held by the supporting member expands to depress and shift the rod. The thus created movement of the rod is detected by a mcroswitch, whereby the rotation of the rotor is interrupted.

7 Claims, 5 Drawing Figures

BLOCKING CONDITION DETECTION DEVICE IN A MEDICAL FLUID INJECTION SYSTEM

BACKGROUND AND SUMMARY OF THE INVENTION

The present invention relates to a medical fluid injection system for injecting a medical fluid into a vein through the use of an injection pump.

The present invention relates, more particularly, to a detection device for detecting a blocking condition in a flexible conduit connected to an injection pump in a medical fluid injection system.

A medical fluid injection system must ensure high safety because the medical fluid injection system is applied to the human body. A flexible conduit such as a vinyl tube is usually employed in the medical fluid injection system for supplying the medical fluid derived from an injection pump. It is strictly required that an undesirable blocking condition of the flexible conduit be accurately detected.

Accordingly, an object of the present invention is to enhance the safety of a medical fluid injection system.

Another object of the present invention is to provide a novel detection system for detecting an undesirable blocking condition in a flexible conduit in a medical fluid injection system.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

To achieve the above objects, pursuant to an embodiment of the present invention, a portion of a flexible conduit is held by a conduit supporting member so that the section of the flexible conduit substantially shows an ellipse configuration or a rectangular configuration. A rod is slidably disposed in the conduit supporting member so that one end of the rod contacts the peripheral surface of the flexible conduit. When an undesirable blocking condition occurs in the flexible conduit, the flexible conduit is expanded to shift the rod. The shift movement of the rod is detected by a detection system to interrupt the supply of the medical fluid.

BRIEF DESCRIPTION OF THE DRAWINGS

The present invention will be better understood from the detailed description given hereinbelow and the accompanying drawings which are given by way of illustration only, and thus are not limitative of the present invention and wherein.

DESCRIPTION OF THE PREFERRED EMBODIMENTS

Figure 1:
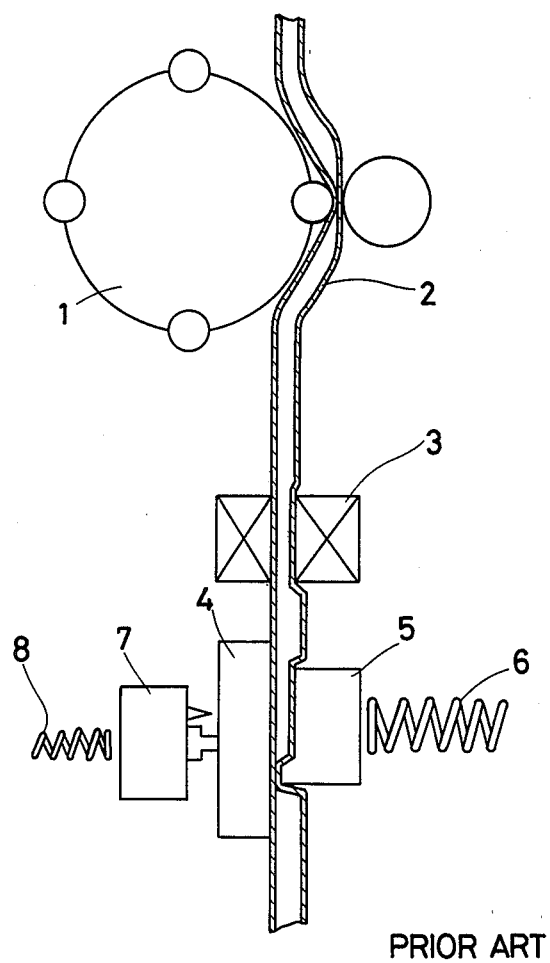
FIG. 1 is a schematic sectional view of an essential part of a conventional medical fluid injection system.

FIG. 1 shows a conventional medical fluid injection system. A medical fluid of a predetermined flow rate is supplied downward to the human body by the rotation of a rotor 1 through a flexible conduit 2 such as a vinyl tube. An optical air sensor 3 is disposed for detecting whether air bubbles are mixed with the medical fluid. If the optical air sensor 3 detects that the air bubbles are mixed with the medical fluid, the rotation of the rotor 1 is interrupted to terminate the supply of the medical fluid.

A stationary supporting plate 4 and a movable clamp 5 are disposed to sandwich the flexible conduit 2 in order to prevent the gravity flow of the medical fluid when the rotor 1 is not rotated. That is, it is not desirable that the medical fluid contained in the flexible conduit 2 flows to the human body due to the gravity when the rotor 1 is not rotating. The movable clamp 5 is depressed toward the stationary supporting plate 4 through the use of a clamp bias spring 6.

When the rotor 1 is not rotating, the flexible conduit 2 is normally blocked by the stationary supporting plate 4 and the movable clamp 5 by means of the clamp bias spring 6. When the rotor 1 is rotating, the pressurized medical fluid functions to depress the movable clamp 5 to the right in FIG. 1 against the clamp bias spring 6. Therefore, the medical fluid flows to the human body through the clearance formed in the flexible conduit 2.

A microswitch 7 is supported by a support spring 8, which has a spring force smaller than the clamp bias spring 6, in such a manner that the microswitch 7 follows the movement of the movable clamp 5. More specifically, the microswitch 7 is depressed to the right in FIG. 1 so that a rod connected to the microswitch 7 always contacts the movable clamp 5. When an undesirable blocking condition occurs in the flexible conduit 2, the increased pressure in the flexible conduit 2 functions to expand the flexible conduit 2. The expanding movement of the flexible conduit 2 functions to shift right the movable clamp 5 beyond a preselected range. Accordingly, an actuator of the microswitch 7 is made to contact with the stationary supporting plate 4 to switch on the microswitch 7. The thus obtained switching signal is applied to a control circuit to indicate the undesirable blocking condition and to interrupt the further rotation of the rotor 1.

The above discussed gravity flow preventing operation and undesirable blocking condition detection operation will be described, in detail, with reference to FIG. 2.

Figure 2:
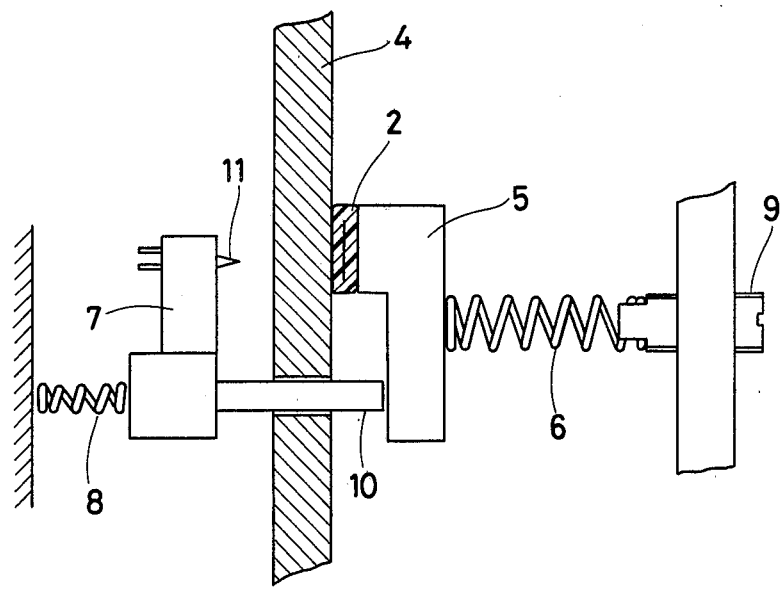
FIG. 2 is a sectional view for explaining an operation mode of the medical fluid injection system of FIG. 1.

When the rotor 1 is not rotating, the flexible conduit 2 is blocked by the stationary supporting plate 4 and the movable clamp 5 as shown in FIG. 2. When the rotor 1 is rotating, the fluid pressure in the flexible conduit 2 depresses the movable clamp 5 to provide a clearance in the flexible conduit 2. An adjusting screw 9 is secured to the spring 6 to adjust the spring force of the spring 6 so that the system functions in a manner as discussed above. A slidable rod 10 is fixed to the microswitch 7. The slidable rod 10 is slidably secured through the stationary supporting plate 4 so that the end of the slidable rod 10 contacts the movable clamp 5 by means of the spring 8.

When the rotor 1 rotates, the movable clamp 5 is shifted to the right against the spring 6 to allow the medical fluid to flow toward the human body. At this moment, the microswitch 7 is also shifted to the right by the shift length of the movable clamp 5, but an actuator 11 of the microswitch 7 does not yet make contact with the stationary supporting plate 4. When an undesirable blocking condition occurs in the flexible conduit 2, the movable clamp 5 is shifted further to the right due to the expanding movement of the flexible conduit 2. Thus, the microswitch 7 is also shifted to the right beyond a preselected range so that the actuator 11 makes contact with the stationary supporting plate 4. Thus, in this manner the microswitch 7 detects the undesirable blocking condition.

The above-mentioned conventional system does not show a high degree of reliability. The spring 6 has to exert a considerably large force to ensure the prevention of the gravity flow of the medical fluid. The flexible conduit 2 such as a vinyl tube has a circular cross section and, therefore, the expanding movement is quite small. Accordingly, the undesirable blocking condition cannot be accurately detected in the conventional system. Moreover, it is very difficult to determine a preferred distance between the actuator 11 of the microswitch 7 and the stationary supporting plate 4. In addition to that, when the flexible conduit 2 is blocked by the movable clamp 5 and the stationary supporting plate 4, the distance between the actuator 11 and the stationary supporting plate 4 varies depending on the material of the flexible conduit 2 and the ambient temperature.

Figure 3:
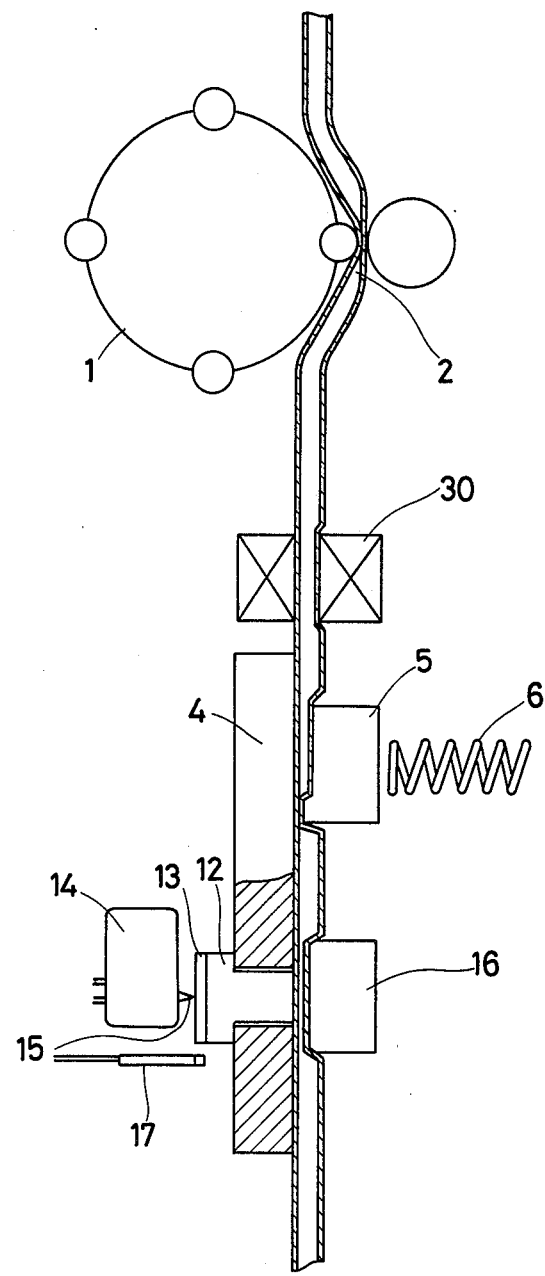
FIG. 3 is a schematic sectional view of an essential part of an embodiment of a medical fluid injection system of the present invention.

FIG. 3 shows an embodiment of a medical fluid injection system of the present invention. Like elements corresponding to those of FIG. 1 are indicated by like numerals.

An ultrasonic air sensor 30 is disposed to detect air bubbles present in the medical fluid. The gravity flow preventing unit includes the stationary supporting plate 4, the movable clamp 5 and the spring 6, and functions in a manner similar to that described with reference to FIG. 1.

The medical fluid injection system of the present invention further includes an undesirable blocking condition detection unit. An opening is formed in the stationary supporting plate 4 through which a rod 12 is slidably disposed so that one end of the rod 12 contacts the flexible conduit 2 which can be a vinyl tube. A magnet 13 is secured to the other end of the rod 12. A microswitch 14 is disposed so that an actuator 15 of the microswitch 14 is made to contact with the magnet 13. More specifically, the actuator 15 functions to depress the rod 12 to the right in FIG. 3, whereby the end of the rod 12 is made to contact with the flexible conduit 2. A stationary clamp 16, and spacers 18 are disposed to sandwich the flexible conduit 2 in combination with the stationary supporting plate 4. The stationary clamp 16 and spacers 18 are shaped so that the section of the flexible conduit 2 substantially shows an ellipse configuration or a rectangular configuration.

When an abnormal blocking condition occurs in the flexible conduit 2, the abnormal pressure in the flexible conduit 2 functions to depress the rod 12 toward the left in FIG. 3. The shift movement of the rod 12 switches on the microswitch 14 thereby interrupting the rotation of the rotor 1. A magnetoresistive element 17 is disposed to detect the shift movement of the magnet 13. That is, the magnet 13 and the magnetoresistive element 17 function, in combination, as a safe unit when the microswitch 14 is not in the normal condition. More specifically, the magnetoresistive element 17 develops a detection output to interrupt the rotation of the rotor 1 when the rod 12 is shifted to the left beyond a preselected shift range.

Figures 4, 5:
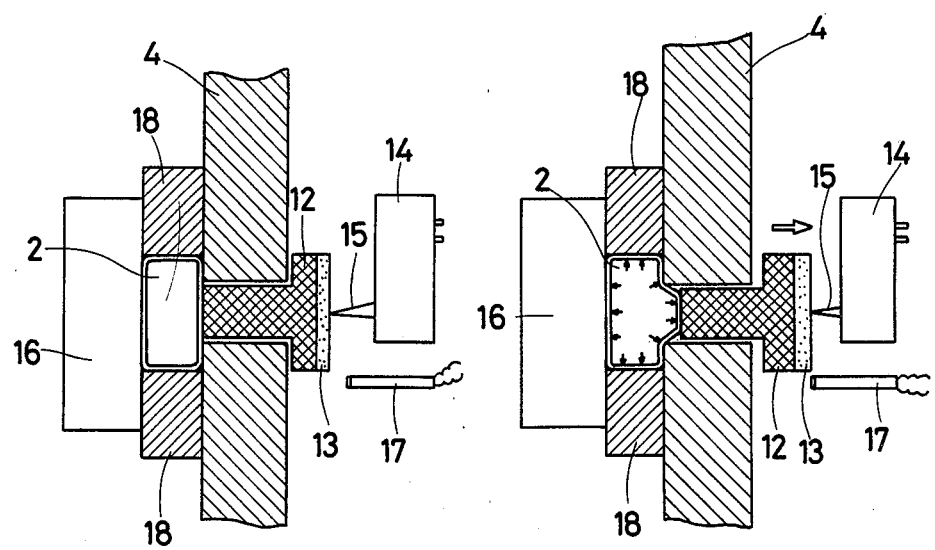
FIGS. 4 and 5 are sectional views for explaining operation modes of the medical fluid injection system of FIG. 3.

FIGS. 4 and 5 show operation modes of the medical fluid injection system of the present invention, wherein FIG. 4 shows a normal condition, and FIG. 5 shows an abnormal blocking condition.

The flexible conduit 2 is surrounded by the stationary supporting plate 4, the stationary clamp 16, the spacers 18, and the end of the rod 12 so that the section of the flexible conduit 12 substantially shows a rectangular configuration as shown in FIG. 4. Since the flexible conduit 2, which normally has a circular section, is forced to have a rectangular section, the expansion of the flexible conduit 2 is easily created toward the rod 12. Accordingly, the undesirable blocking condition of the flexible conduit 2 is accurately and rapidly detected by the microswitch 14 as shown in FIG. 5.

In a preferred form, the stationary clamp 16 and the spacers 18 are integrally formed, and removably secured to the stationary supporting plate 4. In this construction, the flexible conduit 2 is easily exchanged with a new one.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A medical fluid injection system comprising:
a flexible conduit;
supply means for supplying a pressurized medical fluid through said flexible conduit; and
a blocking condition detection means for detecting an abnormal blocking condition in said flexible conduit, said blocking condition detection means including
support means provided with an opening for supporting said flexible conduit, said flexible conduit being conformed by said support means into a substantial rectangular configuration juxtapositioned to said opening,
rod means slidably disposed through said opening; and
detection means for detecting a shift in movement of said rod means;
one end of said rod means being in contact with said flexible conduit at the location of said rectangular configuration and the other end of said rod means being in contact with said detection means such that, upon the detection of a blocking condition within said conduit manifested by an abnormal pressure within said conduit, said flexible tubing expands at the location of said rectangular configuration into said opening so as to depress and shift said rod means to make contact with said detection means, said rectangular configuration increasing the sensitivity of said detection means.

2. The medical fluid injection system of claim 1, further including an ultrasonic air sensor juxtapositioned to said flexible conduit for detecting air bubbles in said medical fluid.

3. The medical fluid injection system of claim 1 or 2 wherein said detection means comprises:
a microswitch.

4. The medical fluid injection system of claim 3, wherein the output signal of said microswitch operatively communicates with said supply means for interrupting the supplying operation when a shift in movement of said rod means is detected.

5. The medical fluid injection system of claim 3, further comprising:
   a magnet secured to said other end of said rod means; and a magnetoresistive element disposed near said the other end of said rod means for detecting a shift in movement of said rod means.

6. A detection system for detecting an abnormal blocking condition in a flexible, tubular conduit through which a pressurized fluid is being supplied, said blocking condition detection system comprising:
   a flexible, tubular conduit means,
   support means provided with an opening for supporting said flexible conduit, said flexible conduit being conformed by said support means into a substantial rectangular configuration juxtapositioned to said opening,
   rod means slidably disposed to said opening, and
   detection means for detecting a shift in movement of said rod means,
   one end of said rod means being in contact with said flexible conduit at the location of said rectangular configuration and the other end of said rod means being in contact with said detection means such that, upon detection of a blocking condition within said conduit manifested by an abnormal pressure within said conduit, said flexible tubing expands at the location of said rectangular configuration into said opening so as to depress and shift said rod means to make contact with said detection means, said rectangular configuration increasing the sensitivity of said detection system.

7. The detection system of claim 6, further comprising:
   a magnet secured to said other end of said rod means, and
   a magnetoresistive element disposed near said other end of said rod means for detecting a shift in movement of said rod means.

* * * * *